United States Patent [19]

Reed

[11] Patent Number: 5,734,033
[45] Date of Patent: Mar. 31, 1998

[54] ANTISENSE OLIGONUCLEOTIDES INHIBITING HUMAN BCL-2 GENE EXPRESSION

[75] Inventor: John Reed, Philadelphia, Pa.

[73] Assignee: The Trustees of the University of Pennsylvania, Philadelphia, Pa.

[21] Appl. No.: 217,082

[22] Filed: Mar. 24, 1994

Related U.S. Application Data

[63] Continuation of Ser. No. 840,716, Feb. 21, 1992, abandoned, which is a continuation-in-part of Ser. No. 288,692, Dec. 22, 1988, abandoned.

[51] Int. Cl.$^6$ .................................................. C07H 21/04
[52] U.S. Cl. ........................... 536/23.1; 536/24.5
[58] Field of Search ........................ 536/23.1, 24.5

[56] References Cited

U.S. PATENT DOCUMENTS 4,806,463  2/1989  Goodchild ................................. 435/5

OTHER PUBLICATIONS

Strasser et al Cell 67: 889, 1991.
Reed et al Can. Res. 50: 6565, 1990.
Williams Cell 65: 1097, 1991.
Tsujimoto et al PNAS 83: 5214, 1986.
Reed et al Science 236: 1295, 1987.
Stein et al. NAR 16(8): 3209, 1988.
Negrini et al Cell 49: 455, 1987.
Stull et al Pharmaceu. Res 12(4): 465, 1995.
Miller et al. Ant Cancer Drug Design. 2: 117, 1987.
Asseline et al., *Proc. Natl Acad. Sci. USA* 81:3297–3301 (1984).
Aviv et al., *Proc. Natl. Acad. Sci. USA*, 69:1408–1412 (1972).
Bishop, "Cellular Oncogenes and Retroviruses", *Science*, 235:305–311 (1987).
Blake et al., *Biochemistry* 24:6132–6138 (1985).
Boutorin et al., *FEBS Letters* 172:43–46 (1984).
Chen and Sigman, *Proc. Natl. Acad. Sci. USA* 83:7147–7151 (1986).
Chu et al., *Proc. Natl. Acad. Sci.* 82:963–967 (1985).
Chomczynski et al., *Analyt. Biochem.*, 162:156–159 (1987).
Croce et al., "Molecular Basis Of Human B and T Cell Neoplasia", in: *Advance in Viral Oncology*, 7:35–51, G. Klein (ed.), New York: Raven Press, 1987.
Halder et al., *Nature* (London), 342:195–197 (1989).
Holt et al., *Mol. Cell Biol.* 8:963–973 (1988).
Kern et al., *J. Clin. Invest.*, 81:237–244 (1988).
Knorre et al., *Biochemie* 67:785–789 (1985).
Morvan et al., *Nucl. Acids Res.*, 14:5019–5032 (1986).
Reed et al., *J. Immunol.*, 134:314–319 (1985).
Reed et al., *J. Immunol.*, 134:1631–1639 (1985).
Reed et al., *Mol. Cell Biol.*, 5:3361–3366 (1985).
Van den Elsen et al., *Nature* 312:413–418 (1984).
Vlassov et al., *Nucl. Acids Res.* 14:4065–4076 (1986).
Webb et al., *Nucl. Acids Res.* 14:7661–7674 (1986).
Weiss et al., *J. Immunol.*, 138:2169–2174 (1987).
Wickstrom et al., *Proc. Natl. Acad. Sci. USA*, 85:1028–1–32 (1988).
Zamecnik and Stephenson, *Proc. Natl. Acad. Sci. USA*, 75:280–284 (1978).
Zamecnik et al., *Proc. Natl. Acad. Sci. USA*, 83:4143–4146 (1986).
John C. Reed et al., "BCL2–mediated tumorigenicity of a human T–lymphoid cell line: Synergy with MYC and inhibition by BCL2 antisense", *Proc Natl. Acad. Sci. USA*, 87:3660–3664 (1990).

*Primary Examiner*—Suzanne E. Ziska
*Attorney, Agent, or Firm*—Oblon, Spivak, McClelland, Maier & Neustadt, P.C.

[57] ABSTRACT

The present invention provides novel antisense oligodeoxynucleotides which are useful in inhibiting lymphoma or leukemia cells. The subject oligodeoxynucleotides are complementary to a strategic site in the mRNA sense strand to the human bcl-2 gene. Such oligodeoxynucleotide are provided either in their native state or as a derivative such as the phosphorothioate. In the preferred embodiments, these antisense oligodeoxynucleotide straddle the predicted translation-initiation site of the mRNA coding strand, the splice donor region, the splice acceptor region of the mRNA coding strand, or the 5'-cap region for the human bcl-2 gene.

13 Claims, 7 Drawing Sheets

ANTISENSE OLIGONUCLEOTIDES INHIBITING HUMAN BCL-2 GENE EXPRESSION

This application is a continuation of Ser. No. 07/840,716, filed Feb. 21, 1992, abandoned, which is a continuation-in-part of Ser. No. 07/288,692, filed Dec. 22, 1988 abandoned.

REFERENCE TO GOVERNMENT GRANTS

The research in this patent application was supported in part by National Institutes of Health grant CA 26380. The United States government has certain rights in the invention.

FIELD OF THE INVENTION

The present invention relates to the field of treatments for cancer and more particularly to the field of antisense oligonucleotide treatments for cancer.

BACKGROUND OF THE INVENTION

Current approaches to cancer treatment suffer from a lack of specificity. The majority of drugs that have been developed are natural products or derivatives that either block enzyme pathways or randomly interact with DNA. Due to low therapeutic indices, most cancer treatment drugs are accompanied by serious dose-limiting toxicities. The administration of drugs to treat cancer kills not only cancer cells but also normal non-cancerous cells. Because of these deleterious effects, treatments that are more specific for cancerous cells are needed.

It has been found that a class of genes, the oncogenes, plays a large role in the transformation and maintenance of the cancerous state and that turning off these genes, or otherwise inhibiting their effects, can return a cell to a normal phenotype. The role of oncogenes in the etiology of many human cancers has been reviewed in Bishop, "Cellular Oncogenes and Retroviruses", Science, 235:305–311 (1987).

Recently, a human gene termed bcl-2 (B cell lymphoma/leukemia-2) has been implicated in the etiology of some common lymphoid tumors, Croce et al., "Molecular Basis Of Human B and T Cell Neoplasia", in: *Advance in Viral Oncology*, 7:35–51, G. Klein (ed.), New York: Raven Press, 1987. High levels of expression of the human bcl-2 gene have been found in all lymphomas with t (14; 18) chromosomal translocations including most follicular B cell lymphomas and many large cell non-Hodgkin's lymphomas. High levels of expression of the bcl-2 gene have also been found in certain leukemias that do not have a t (14; 18) chromosomal translocation, including most acute lymphocytic leukemias of the pre-B cell type.

Antisense oligodeoxynucleotides are one example of a specific therapeutic tool with the potential for ablating oncogene function. These short (usually about 30 bases) single-stranded synthetic DNAs have a complementary base sequence to the target mRNA and form a hybrid duplex by hydrogen bonded base pairing. This hybridization can be expected to prevent expression of the target mRNA code into its protein product and thus preclude subsequent effects of the protein product. Because the mRNA sequence expressed by the gene is termed the sense sequence, the complementary sequence is termed the antisense sequence. Inhibition of mRNA would be more efficient than inhibition of an enzyme's active site, since one mRNA molecule gives rise to multiple protein copies.

Synthetic oligodeoxynucleotides complementary to (antisense) mRNA of the c-myc oncogene have been used to specifically inhibit production of c-myc protein, thus arresting the growth of human leukemic cells in vitro, Holt et al., *Mol. Cell Biol.* 8:963–973 (1988), and Wickstrom et al., *Proc. Natl. Acad. Scio USA*, 85:1028-1-32 (1988). Oligodeoxynucleotides have also been employed as specific inhibitors of retroviruses, including the human immunodeficiency virus (HIV-I), Zamecnik and Stephenson, *Proc. Natl. Acad. Sci. USA*, 75:280–284 (1978) and Zamecnik et al., *Proc. Natl. Acad. Sci. USA*, 83:4143–4146 (1986).

SUMMARY OF THE INVENTION

The invention provides oligodeoxynucleotides and methods for inhibiting growth of lymphoma or leukemia cells, that are types of lymphocytes. An antisense oligodeoxynucleotide complementary to at least an effective portion of the mRNA sense strand to the human bcl-2 gene is provided and cells are then contacted with the antisense oligodeoxynucleotide in a concentration sufficient to inhibit proliferation of the cells. The methods of the invention are suitable for inhibiting proliferation of lymphoma/leukemia cells that express the human bcl-2 gene and have a t (14; 18) chromosomal translocation as well as those that express the bcl-2 gene but do not have a t (14; 18) chromosomal translocation.

In accordance with preferred embodiments, the oligodeoxynucleotide is substantially complementary to a strategic site in the mRNA sense strand. A preferred strategic site is the translation-initiation site of the mRNA coding strand. Alternative strategic sites include coding sites for splicing, transport or degradation. The subject antisense oligodeoxynucleotide either in its "native", unmodified form or as a derivative, is brought into contact with the target lymphoma or leukemia cells. For in vivo therapeutic use, a derivative of the "native" oligodeoxynucleotide, such as the phosphorothioate form is preferred since it is believed that these forms are more resistant to degradation, notwithstanding the fact that response times to some analogues, such as the phosphorothioate analogs, has been found to be somewhat slower than to the "native" form of the oligodeoxynucleotide.

A preferred antisense oligodeoxynucleotide, denominated herein the TI-AS (translation initiation antisense) nucleotide straddles the translation-initiation site of the mRNA coding strand of the human bcl-2 gene and is complementary to this region. More preferably, this nucleotide comprises a TAC portion which is complementary to the ATG initiation sequence of the coding strand for the bcl-2 gene, and preferably further comprises flanking portions of two to about one hundred bases, more preferably from about five to about twenty bases, which are complementary to portions of the bcl-2 gene coding strand flanking said initiation sequence. The TI-AS nucleotide has been found effective at inhibiting the growth of the target cells both in the presence and absence of serum.

Alternatively, the antisense oligodeoxynucleotide comprises an antisense nucleotide complementary to at least an effective portion of the splice donor site of the mRNA coding strand for the human bcl-2 gene. More particularly, this nucleotide comprises a CA portion which is complementary to the GT splice donor of the bcl-2, and again comprises flanking portions of two to about one hundred bases, preferably from about five to about twenty bases, which are complementary to portions of the bcl-2 gene coding strand flanking said splice donor.

In yet another embodiment, the antisense nucleotide is complementary to at least an effective portion of the splice acceptor region of the mRNA coding strand for the human bcl-2 gene. This nucleotide comprises at least a TC portion which is complementary to the AG splice acceptor of the bcl-2 gene, and again comprises flanking portions of two to about one hundred, preferably from about five to about twenty bases which are complementary to portions of the bcl-2 gene coding strand flanking said acceptor. The subject oligodeoxynucleotide may also be selected to overlap the coding site for the 26 kDa protein, bcl-2-alpha or for the 22 kDa protein, bcl-2-beta, protein products of the bcl-2 gene. Preferably the oligodeoxynucleotide is selected to minimize homology with antisense nucleotides for mRNA coding strands for other gene sequences.

Accordingly, a primary object of the present invention is the provision of novel antisense oligodeoxynucleotides which are useful in inhibiting the growth of leukemia and/or lymphoma cells. A further object of the present invention is the provision of methods for inhibiting the growth of leukemia and/or lymphoma cells using said oligodeoxynucleotides. These and other objects of the present invention will become apparent from the following, more detailed description.

BRIEF DESCRIPTION OF THE DRAWINGS

FIG. 4 (a) shows the effect of oligonucleotides targeted against the translation initiation site. FIG. 4 (b) shows the effect of oligonucleotides directed against the 5'-cap region of bcl-2 mRNA.

DETAILED DESCRIPTION OF THE PREFERRED EMBODIMENTS

Figure 1A:
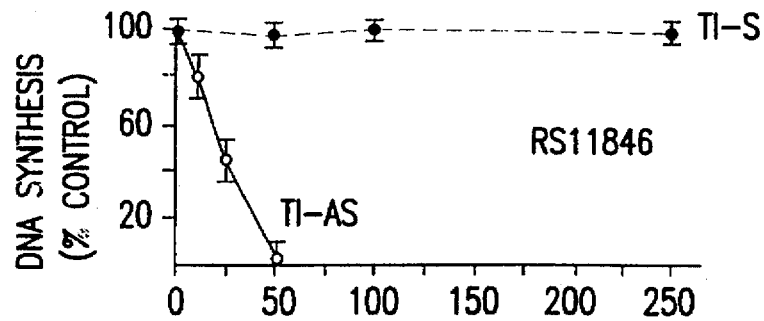
FIG. 1 shows graphs of the effects of varying concentrations of oligodeoxynucleotides on inhibition of cell proliferation.
Figure 1B:
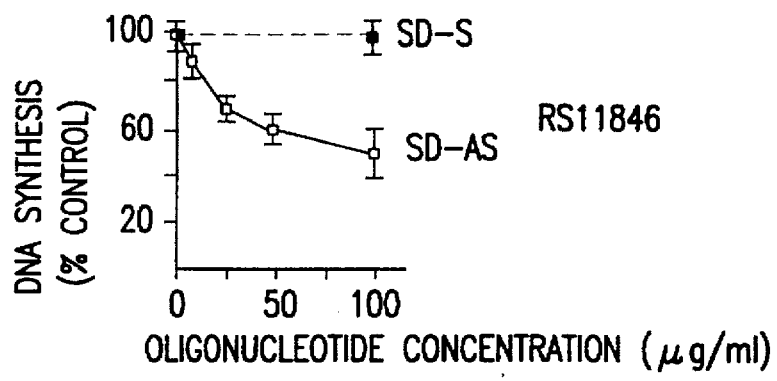
Figure 1C:
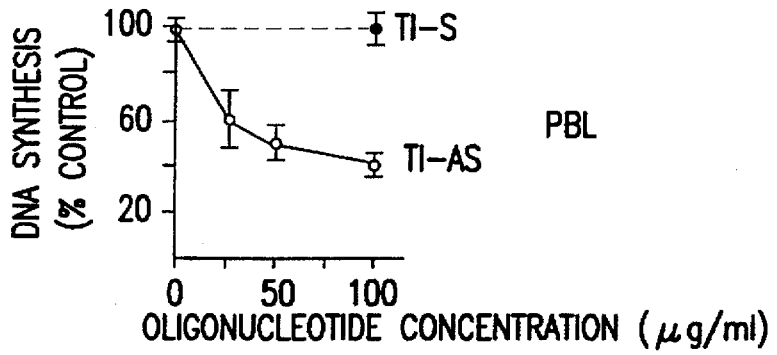
Figure 1D:
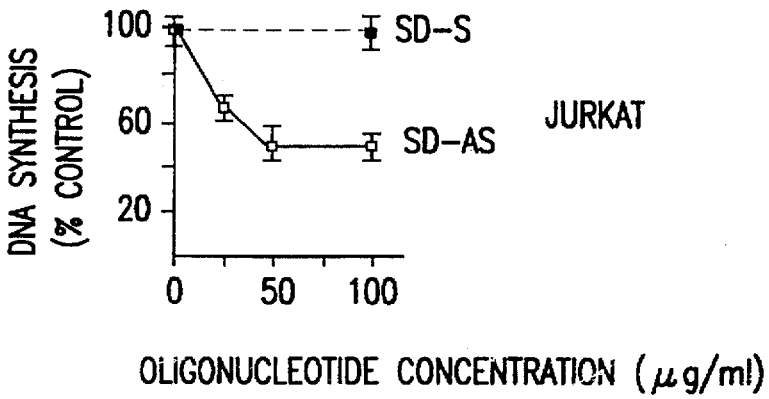

Oligodeoxynucleotides are selected for use in the invention according to their ability to inhibit cell proliferation. Uncontrolled cell proliferation is a marker for a cancerous or abnormal cell type. Normal, non-cancerous cells divide regularly, at a frequency characteristic for the particular type of cell. When a cell has been transformed into a cancerous state, the cell divides and proliferates uncontrollably. Inhibition of proliferation modulates the uncontrolled division of the cell. Containment of cell division often correlates with a return to a non-cancerous state.

Oligodeoxynucleotides suitable for use in the invention are preferably two to two hundred nucleotide bases long; more preferably ten to forty bases long; most preferably twenty bases long. The oligodeoxynucleotides are preferably selected from those oligodeoxynucleotides complementary to strategic sites along the mRNA of bcl-2, such as the translation initiation site, donor and acceptor splicing sites, or sites for transportation or degradation. Blocking translation at such strategic sites prevents formation of a functional bcl-2 gene product. It should be appreciated, however, that any combination or subcombination of nucleotides complementary or substantially complementary to the bcl-2 mRNA that inhibits cell proliferation is suitable for use in the invention. For example, oligodeoxynucleotides complementary to non-contiguous stretches of the bcl-2mRNA may inhibit cell proliferation and would thus be suitable for use in the invention. It should also be appreciated that oligodeoxynucleotides suitable for use in the invention may also include nucleotides flanking those complementary or substantially complementary to the strategic or other sites along the bcl-2 mRNA. The flanking portions are preferably from two to about one hundred bases, more preferably from about five to about twenty bases in length. It is also preferable that the oligodeoxynucleotide be complementary to a portion of the mRNA that is not commonly found in mRNA of other genes to minimize homology of antisense nucleotides for mRNA coding strands from other genes.

Preferred antisense, or complementary, oligodeoxynucleotides are listed in Table 1.

TABLE 1

| bcl-2 Oligodeoxynucleotides | | |
|---|---|---|
| transition initiation | | |
| antisense (TI-AS) | 3'... CCCTTCCTACCGCGTGCGAC ... 5' (SEQ ID NO: 1) | |
| bcl-2 splice donor | 5'... CTTTTCCTCTGGGAAGGATGGCGCACGCTGGGAGA ... 3' | (SEQ ID NO: 2) |
| antisense (SD-AS) | 3'... CCTCCGACCCATCCACGTAG ... 5' (SEQ ID NO: 3) | |
| bcl-2 splice acceptor | 5'... ACGGGGTAC ... GGAGGCTGGGTAGGTGCATCTGGT ... 3' | (SEQ ID NO: 4) |
| antisense (SA-AS) | 3'... GTTGACGTCCTACGGAAACA ... 5' (SEQ ID NO: 5) | |
| bcl-2 | 5'... CCCCCAACTGCAGGATGCCTTTGTGGAACTGTACGG ... 3' | (SEQ ID NO: 6) |

FIGS. 6 (a) and (b) are graphs showing the results of immunofluorescence analysis of bcl-2 protein levels in oligonucleotide-treated cells.

FIGS. 7 (a)–(d) are FACS profiles for 697 cells before and after treatment with bcl-2 antisense oligonucleotides.

It will be appreciated by those skilled in the art to which this invention pertains, that oligodeoxynucleotides having a greater or lesser number of substituent nucleotides, or that extend further along the bcl-2 mRNA in either the 3' or 5' direction than the preferred embodiments, but which also inhibit cell proliferation are also within the scope of the invention.

It is preferable to use derivatives of antisense oligodeoxynucleotides in the performance of the invention rather than "native" or unmodified oligodeoxynucleotides. "Native" oligodeoxynucleotides can be conveniently synthesized with a DNA synthesizer using standard phosphoramidite chemistry. Suitable derivatives, and methods for preparing the derivatives, include phosphorothioate, Stein et al., *Nucl. Acids Res.*, 16:3209–3221 (1988); methylphosphonate, Blake et al., *Biochemistry* 24:6132–6138 (1985) and alpha-deoxynucleotides, Morvan et al., *Nucl. Acids Res.*, 14:5019–5032 (1986) and covalently-linked derivatives such as acridine, Asseline et al., *Proc. Natl Acad. Sci. USA* 81:3297–3301 (1984); alkylated (e.g., N-2-chloroethylamine), Knorre et al., *Biochemie* 67:785–789 (1985) and Vlassov et al., *Nucl. Acids Res.* 14:4065–4076 (1986); phenazine, Knorre et al., supra, and Vlassov et al., supra; 5-methyl-$N^4$-$N^4$-ethano-cytosine, Webb et al., *Nucl. Acids Res.* 14:7661–7674 (1986); Fe-ethylenediamine tetraacetic acid (EDTA) and analogues, Boutorin et al., *FEBS Letters* 172:43–46 (1984); 5-glycylamido-1, 10-O-phenanthroline, Chi-Hong et al., *Proc. Natl. Acad. Sci. USA* 83:7147–7151 (1986); and diethylenetriamine-pentaacetic acid (DTPA) derivatives, Chu et al., *Proc. Natl. Acad. Sci. USA* 82:963–967 (1985). All of the above publications are hereby specifically incorporated by reference as if fully set forth herein.

The oligodeoxynucleotides may be administered to patients by any effective route, including intravenous, intramuscular, intrathecal, intranasal, intraperitoneal, subcutaneous injection, in situ injection and oral administration. The oligodeoxynucleotides may be mixed with an amount of a physiologically acceptable carrier or diluent, such as a saline solution or other suitable liquid. The oligodeoxynucleotides may also be combined with liposomes or other carriers.

The oligodeoxynucleotides may also be useful for ex vivo bone marrow purging. Normally, the amounts of conventional chemotherapeutic drugs and irradiation that a patient can receive are limited by toxicity to the marrow, i.e., anemia (fatigue, heart failure), thrombocytopenia (bleeding), neutropenia (infection). Thus, in order to deliver sufficient concentrations of drugs and irradiation to totally eradicate the tumor, the physician would simultaneously destroy the patient's normal bone marrow cells leading to patient demise. Alternatively, large amounts of bone marrow can be surgically extracted from the patient and stored in vitro, while the patient receives aggressive conventional treatment. The patient can then be rescued by reinfusion of their own bone marrow cells, but only if that marrow has been "purged" of residual malignant cells. Antisense reagents employing the oligodeoxynucleotides of the invention could be used to remove residual malignant cells from the bone marrow.

The oligodeoxynucleotides are administered in amounts effective to inhibit leukemia/lymphoma cell proliferation. The actual amount of any particular oligodeoxynucleotide administered will depend on factors such as the type of lymphoma/leukemia, the toxicity of the oligodeoxynucleotide to other cells of the body, its rate of uptake by leukemia/lymphoma cells, and the weight and age of the individual to whom the oligodeoxynucleotide is administered. Because of inhibitors present in human serum that may interfere with the action of the oligodeoxynucleotides, an effective amount of the oligodeoxynucleotides for each individual may vary. An effective dosage for the patient can be ascertained by conventional methods such as incrementally increasing the dosage of the oligodeoxynucleotide from an amount ineffective to inhibit cell proliferation to an effective amount. It is expected that concentrations presented to leukemia/lymphoma cells in the range of about 10 to about 400 micromolar, more preferably in the range of from about 20 micromolar to about 250 micromolar, will be effective to inhibit cell proliferation.

The oligodeoxynucleotides are administered to the patient for at least a time sufficient to inhibit proliferation of the lymphoma/leukemia cells. The oligodeoxynucleotides are preferably administered to patients at a frequency sufficient to maintain the level of oligodeoxynucleotides at an effective level in or around the lymphoma/leukemia cells. To maintain an effective level, it may be necessary to administer the oligodeoxynucleotides several times a day, daily or at less frequent intervals. Oligodeoxynucleotides are administered until lymphoma-leukemia cells can no longer be detected, or have been reduced in number such that further treatment provides no significant reduction in number, or the cells have been reduced to a number manageable by surgery or other treatments. The length of time that the oligodeoxynucleotides are administered will depend on factors such as the rate of uptake of the particular oligodeoxynucleotide by lymphoma/leukemia cells and time needed for the cells to respond to the oligodeoxynucleotide. In vitro, maximal inhibition of leukemic cell proliferation by "native", unmodified antisense oligodeoxynucleotides occurred two days after initiation of cultures, whereas phosphorothioate oligodeoxynucleotides required 4 to 7 days to achieve maximal inhibition. In vivo, the time necessary for maximal inhibition of cell proliferation may be shorter or longer.

The oligodeoxynucleotides of the invention may be administered to patients as a combination of two or more different antisense oligodeoxynucleotide sequences or as a single type of sequence. For instance, TI-AS and SD-AS could be administered to a patient or TI-AS alone.

It is also believed that the oligodeoxynucleotides of the invention may be useful in the treatment of autoimmune diseases. Autoimmune diseases are those diseases in which the body's immune system has malfunctioned in some way. Administration of the oligodeoxynucleotides of the invention to a person having an autoimmune disease should inhibit proliferation of lymphocytes which would in turn reduce the symptoms of the autoimmune disease. For use in treating autoimmune diseases, the oligodeoxynucleotides would be administered as described herein.

EXPERIMENTAL

Preparation of Oligodeoxynucleotides

Normal and phosphorothioate oligodeoxynucleotides were synthesized using an Applied Biosystems 380B DNA synthesizer, and purified by HPLC reverse-phase chromatography (PRP-1 column) as described in Stein et al., *Nucl. Acids Res.*, 16:3209–3221 (1988) which is specifically incorporated as if fully set forth herein. In some cases it was necessary to further purify oligodeoxynucleotides by C18-Sep-Pak chromatography (Waters Associates, Millipore, Inc.), as described previously in Kern et al., *J. Clin. Invest.*, 81:237–244 (1988), to eliminate nonspecific cytotoxic activity. Oligodeoxynucleotides eluted in 30% acetonitrile were evaporated to dryness, resuspended at 1–2 mM in sterile Dulbecco's phosphate-buffered saline or Hanks' buffered salt solution (both from Gibco), and stored at −80° C. in small aliquots.

Cells and Cell Cultures

Human leukemic cells lines used for these studies were RS11846 follicular lymphoma cells, 697 pre-B cell acute lymphocytic leukemic cells, and JURKAT T cell acute lymphocytic leukemic cells as described in Tsujimoto et al., *Proc. Natl. Acad. Sci. USA*, 83:5214–5218 (1986) and Weiss et al., *J. Immunol.*, 138:2169–2174 (1987). Human peripheral blood lymphocytes (PBL) were isolated from fresh whole blood as described in Reed et al., *J. Immunol.*, 134:314–319 (1985). All lymphcid cells were cultured at $5\times10^5$ cells/ml in RPMI medium supplemented with 1 mM glutamine, antibiotics, and either 5–10% (v:v) fetal bovine serum (FBS), 5–10% (v:v) calf serum (CS) (both from Hyclone Laboratories), or 1% (v:v) HLI concentrated supplement (Ventrex Laboratories) for serum-free cultures. Murine fibroblast cell lines were added at $10^3$ cells/cm$^2$ in DMEM medium containing glutamine, antibiotics and 5–10% (v:v) FCS. Fibroblast cell lines were NIH 3T3 cells, 3T3-B-alpha-S cells, and 3T3-B-alpha-AS cells. These latter two cell lines are NIH 3T3 cells that express high levels of a human bcl-2-alpha cDNA in either the sense or antisense orientation, respectively, by virtue of stable transfection with expression vectors constructs.

Measurement of Cellular Proliferation

Proliferation of cell lines cultured in the presence or absence of oligodeoxynucleotides was measured by two methods: cell counts using a hemocytometer; and DNA synthesis by assaying [$^3$H]-thymidine incorporation essentially as described in Reed et al., *J. Immunol.*, 134:314–319 (1985). Briefly, cells were cultured in 96-well flat-bottomed microtiter plates (Falcon) at 0.2 ml/well. At appropriate times, cells were resuspended, 25 µl removed from cultures for cell counting, and this volume replaced with 25 µl of 20 uCi/ml [$^3$H]-thymidine (specific activity 6.7 Ci/mmole) (New England Nuclear). Microtiter cultures were then returned to 37° C. and 95% air: 5% $CO_2$ atmosphere for 8 hours before lysing cells on glass filters and determining relative levels of [$^3$H]-thymidine incorporation into DNA by scintillation counting. Cell counts were performed in the presence of trypan blue dye to determine the concentration of viable cells in duplicate microcultures.

RNA Blot Analysis

Total cellular RNA was isolated by a guanidine-isothiocyanate/phenol procedure as described in Chomczynski et al., *Analyt. Biochem.*, 162:156–159 (1987). The polyadenylated fraction was purified by oligodeoxythymidine-cellulose chromatography as described in Aviv et al., *Proc. Natl. Acad. Sci. USA*, 69:1408–1412 (1972). Approximately 5 µg aliquots of mRNA were size-fractionated in 0.8% agarose/6% formaldehyde gels and transferred to nylon membranes. Blots were prehybridized, hybridized, and washed exactly as described in Reed et al., *Mol. Cell Biol.*, 5:3361–3366 (1985), using either a $^{32}$P-cDNA for human bcl-2, as described in Tsujimoto et al., *Proc. Natl. Acad. Sci. USA*, 83:5214–5218 (1986), or a murine bcl-2 probe, pMBCL5.4 as described in Negrini et al., *Cell*, 49:455–463 (1987). Blots were exposed to Kodak XAR film with intensifying screens at −70° C. for 1–10 days. Eluting $^{32}$P-bcl-2 probes from membranes and rehybridizing with a $^{32}$p probe for mouse beta-2-microglobulin verified nearly equivalent amounts of mRNA for all samples on blots.

RESULTS

Synthetic Oligodeoxynucleotides

Table 1 shows the oligodeoxynucleotides synthesized and their relation to the sense-strand of the human bcl-2 gene. Portions of the sequence of the coding strand of the human bcl-2 gene are shown, including the translation initiation site (top), splice donor site (middle), and splice acceptor region (bottom).

The sequences of the oligodeoxynucleotides synthesized for these investigations are presented, and their relation to human bcl-2mRNA is indicated. The TI-AS oligodeoxynucleotide is antisense at the translation initiation site and TI-S is its complementary sense version. SD-AS and SD-S are oligodeoxynucleotides having antisense and sense orientations, respectively, relative to the splice donor region.

The oligodeoxynucleotide TI-AS straddles the predicted translation-initiation site of bcl-2 mRNAs and is complementary (antisense) to this region. As a control, the sense version of this 20 bp oligodeoxynucleotide, TI-S, was also synthesized.

In an effort to specifically block splicing of bcl-2 mRNAs, a 20 bp antisense oligodeoxynucleotide, SD-AS, was synthesized that overlaps the splice donor site in bcl-2 primary transcripts. In addition, a complementary sense oligodeoxynucleotide, SD-S, was prepared as depicted in Table 1. The human bcl-2 gene gives rise to several transcripts through alternative splice site selections, see Tsujimoto et al., *Proc. Natl. Acad. Sci. USA*, 83:5214–5218 (1986). The preponderance of these transcripts depend upon splicing and encode a 26 kDa protein, bcl-2-alpha. One minor transcript, however, does not undergo a splice and consequently encodes a 22 kDa protein bcl-2-beta. The SD-AS oligodeoxynucleotide can thus potentially block maturation of most but not all bcl-2 transcripts.

Treatment of Serum for In Vitro Investigations of Antisense Normal Oligodeoxynucleotides Because normal oligodeoxynucleotides are sensitive to degradation by nucleases present in serum, the efficacy of the TI-AS oligodeoxynucleotide in fetal bovine serum (FBS) heated for 30 minutes at 56° C. (the usual procedure for inactivating serum complement) was contrasted with the efficacy of TI-AS in FBS heated for 1 hour at 68° C., a temperature sufficient for irreversible inactivation of many nucleases. The RS11846 follicular lymphoma cell line was used. RS11846 cells contain a t (14; 18) chromosomal translocation that deregulates bcl-2 expression, resulting in the accumulation of high levels of bcl-2 mRNAs, Tsujimoto et al., *Proc. Natl. Acad. Sci. USA*, 83:5214–5218 (1986).

RS11846 follicular lymphoma cells were cultured in medium containing 5% (vol:vol) fetal bovine serum (FBS) that had been heated at 56° C. for 0.5 hours or at 68° C. for 1 hour. TI-AS normal oligodeoxynucleotide was added at the initiation of culture, and the density of viable cells determined two days later.

The TI-AS normal oligodeoxynucleotide was more effective in 68° C.-treated serum at suppressing the growth in culture of these lymphoma cells. In all subsequent experiments, sera heated at 68° C. for 1 hour prior to use were used in cultures. This treatment did not impair the growth-supporting capacity of the sera.

Specific Inhibition of Lymphoid Cell Growth by Antisense Normal Oligodeoxynucleotides Antisense normal oligodeoxynucleotides directed against the translation initiation site (TI-AS) and the splice donor site (SD-AS) of bcl-2 transcripts were tested for their ability to suppress the proliferation of normal and neoplastic lymphoid cells.

RS11846 follicular lymphoma cells, JURKAT T cell leukemia cells, and freshly isolated peripheral blood lymphocytes were cultured in medium containing 10% (vol:vol) FBS that had been heated at 68° C. for one hour. Various concentrations of normal oligodeoxynucleotides were added at the initiation of culture, including: TI-AS, TI-S, SD-AS, and SD-S. Relative DNA synthesis was measured in cultures after 2–3 days by [$^3$H]-thymidine incorporation. Data were calculated as a percentage of control cultures containing volumes of PBS or HBSS equivalent to oligodeoxynucleotide-treated cultures, and represent the mean (± standard deviation) of duplicate cultures.

Similar data were obtained by measuring cell counts, excluding cold thymidine inhibition as an explanation for the suppression of DNA synthesis observed in cultures treated with antisense oligodeoxynucleotides.

As shown in FIG. 1, both the TI-AS and SD-AS oligodeoxynucleotides inhibited the growth of RS11846 cells in a concentration-dependent manner. The SD-AS oligonucleotide was less effective in inhibiting cell growth than the TI-AS oligodeoxynucleotide. In contrast to these antisense oligodeoxynucleotides, sense oligodeoxynucleotides (TI-S and SD-S) were not inhibitory even at concentrations of up to 250 µg/ml. Moreover, non-sense oligodeoxynucleotides (i.e., those having the same base composition as the antisense oligodeoxynucleotides but with scrambled sequences) also failed to suppress the proliferation of RS11846 cells. The data thus indicate that antisense oligodeoxynucleotides can specifically block the proliferation of these tumor cells. Several other leukemic cell lines that express the bcl-2 gene were also tested for inhibition of their proliferation by TI-AS and SD-AS oligonucleotides. As with the JURKAT T cell acute lymphocytic leukemic cells, in every case a specific and concentration-dependent decrease in the growth of these human leukemic cells in cultures containing antisense oligodeoxynucleotides was observed.

It has been demonstrated that bcl-2 expression is transiently induced in normal human peripheral blood lymphocytes (PBL) when these cells are stimulated to proliferate, suggesting that this gene may play a role in the regulation of normal lymphocyte growth, Reed et al., *Science* 236:1295–1297 (1987). The capacity of antisense oligodeoxynucleotides to impair the growth of PBL cultured with a monoclonal antibody, OKT3 (Van den Elsen et al., *Nature* 312:413–418 (1984)), that stimulates their proliferation was therefore tested. PBL were stimulated with 50 ng/ml of purified OKT3 monoclonal antibody. As shown in FIG. 1, the TI-AS oligodeoxynucleotide specifically suppressed the proliferation of PBL in a concentration-dependent manner. These antisense normal oligodeoxynucleotides thus suppressed the growth in culture of leukemic cells that constitutively express the bcl-2 gene and of normal lymphocytes wherein bcl-2 expression is inducible.

Time-course of Inhibition by Antisense Normal Oligodeoxynucleotides

The kinetics of inhibition by antisense oligodeoxynucleotides was examined in cultures of RS11846 follicular lymphoma cells and of 697 pre-B cell acute lymphocytic leukemia cells. Both of these neoplastic B cell lines transcribe and accumulate bcl-2 mRNAs at high levels, Tsujimoto et al., *Proc. Natl. Acad. Sci. USA*, 83:5214–5218 (1986).

RS11846 follicular lymphoma and 697 pre-B cell leukemia cells were cultured in medium containing 10% (vol:vol) 68° C.-treated FBS and normal oligodeoxynucleotides. Cells were cultured with 50 µg/ml TI-AS, 100 µg/ml SD-AS, 50 µg/ml TI-S (RS11846 cells) or 100 µg/ml SD-S (697 cells), or PBS as a control. DNA synthesis (kcpm/10$^6$ viable cells) and cell densities (10$^6$ viable cells/ml) were measured at various times after initiation of cultures.

Antisense normal oligodeoxynucleotides markedly inhibited DNA synthesis measured in cultures of these cells within 24 hours. Diminished cell densities were readily apparent in these cultures within 2 days. Antisense normal oligodeoxynucleotides thus rapidly inhibited the in vitro growth of leukemic cells. The action of antisense oligodeoxynucleotides was specific, since sense oligodeoxynucleotides did not impair proliferation in these cultures. Though cell viabilities often declined during the later days of culture no increase in cell death was seen during the first 1–2 days of culture with antisense oligodeoxynucleotides, suggesting a non-cytotoxic mechanism.

Comparison of Different Serum Preparations

Inhibition of proliferation of leukemic cells with antisense oligodeoxynucleotides can vary greatly depending on the lot of serum used in cultures.

To determine the effects of serum of inhibition of proliferation, relative levels of DNA synthesis were measured in cultures of 697 pre-B cell leukemia cells 2 days after addition of 200 µM TI-AS normal oligodeoxynucleotide. Cells were cultured in medium supplemented with 1% (vol:vol) HL1-concentrate (serum-free condition), 5% (vol:vol) of two different lots of calf serum (CS1 and CS2), or 5% (vol:vol) of two different lots of fetal bovine serum (FBS1 and FBS2). All sera were heated at 68° C. for 1 hour prior to use in cultures.

The normal TI-AS oligodeoxynucleotide markedly inhibited DNA synthesis (92%) and cellular proliferation in serum-free cultures (HL1) of 697 cells. This antisense oligodeoxynucleotide was equally effective (94%) in cultures containing 5% (v:v) of one of the lots of fetal bovine serum (FBS2). In contrast, inhibition was significantly reduced in cultures containing other serum preparations (CS1, CS2, FBS1). It has been generally observed that antisense normal oligodeoxynucleotides are less effective in cultures supplemented with calf serum (CS) than in those containing fetal bovine serum (FBS).

Concentration Dependence of Inhibition by Antisense Normal Oligodeoxynucleotides in Serum-free Cultures 697 pre-B cell leukemia cells were cultured in medium with either 1% (vol:vol) HL1-concentrate (serum-free conditions or 5% (vol:vol) 68° C.-treated FBS2). Relative levels of DNA synthesis and cellular densities measured after 2 days in cultures containing various concentrations of normal TI-AS oligodeoxynucleotide.

The TI-AS oligodeoxynucleotide was inhibitory at lower concentrations when used in serum-free cultures. At 100 µM, for instance, no inhibition of cellular proliferation was seen in FBS2-containing cultures, whereas cell counts were reduced by approximately 75% in serum-free cultures. At higher concentrations of antisense oligodeoxynucleotide (200–250 µM), however, inhibition of 697 cellular proliferation was comparable in both types of cultures. The increased efficacy of normal oligodeoxynucleotides in serum-free cultures was specific, since the sense oligonucleotide (TI-S) was not inhibitory at the same concentrations.

Antisense Phosphorothioate Oligodeoxynucleotides: Time-Course of Inhibition

To contrast the efficacy of phosphorothioate oligodeoxynucleotides with that of normal oligonucleotides with regard to inhibition of human leukemic cell growth, phosphorothioate oligodeoxynucleotides were cultured with 697 pre-B cell leukemia cells and the effects on inhibition were measured. 697 pre-B cell leukemia cells were cultured in serum-free medium for various times before measuring DNA synthesis (kcpm) and cell densities ($10^6$ cells/ml). Cells were seeded at an initial density of either $0.2 \times 10^6$ cells/ml or $0.5 \times 10^6$ cells/ml. Culture conditions were 25 µM TI-AS phosphorothioate, 25 µM TI-S phosphorothioate, and control cultures treated with HBSS.

To avoid experimental variation due to differences among lots of sera, 697 leukemic cells were cultured in serum-free conditions. When cultured at an initial seeding density of $0.5 \times 10^6$ cells/ml, 697 cells achieved maximal DNA synthesis and cellular densities at 4–5 days. Addition of 25 µM sense phosphorothioate oligodeoxynucleotide (TI-S) at the initiation of these cultures had little effect on 697 cell growth. In replicate cultures containing 25 µM antisense phosphorothioate (TI-AS), however, some diminution in DNA synthesis was evident within 2 days and was maximal at 4–5 days. Maximal inhibition of 697 cell growth, as determined by cell counts, was seen at 6 days after initiation of cultures.

When 697 cells were initially seeded at $0.2 \times 10^6$ cells/ml, the antisense phosphorothioate oligodeoxynucleotide, TI-AS, resulted in only slight inhibition at 2 days, attaining maximal suppression of DNA synthesis in these cultures at day 7. As with normal oligodeoxynucleotides, this inhibition by phosphorothioate oligodeoxynucleotides appeared to be mediated through non-cytotoxic mechanisms, since cellular viabilities did not decline until late in the course of culture. Compared with normal antisense oligodeoxynucleotides, therefore, phosphorothioate oligodeoxynucleotides had a slower onset of action.

Concentration Dependence of Inhibition by Antisense bcl-2 Phosphorothioate Oligodeoxynucleotides The concentration dependence of inhibition by phosphorothioate and normal TI-AS oligodeoxynucleotides in cultures of 697 cells in serum-free medium was compared as follows.

697 cells were cultured in serum-free medium for either 3 days (normal oligodeoxynucleotides) or 4 days (phosphorothioate oligodeoxynucleotides) prior to measuring cell densities and levels of DNA synthesis. Oligodeoxynucleotide additions to cultures included TI-AS phosphorothioate, TI-S phosphorothioate, TI-AS normal, and TI-S normal.

Figure 2A:
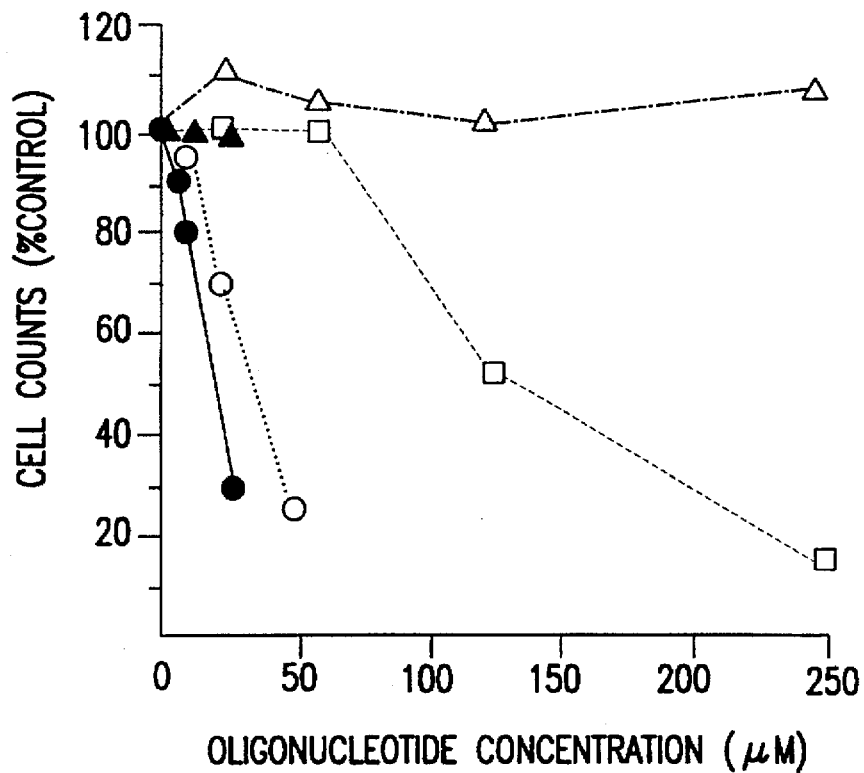
FIG. 2 shows graphs of the concentration dependence of inhibition of cell proliferation by antisense normal and phosphorothioate oligodeoxynucleotides. Oligodeoxynucleotide additions to cultures included TI-AS phosphorothioate (o and ●; two separate experiments), TI-S phosphorothioate (Δ), TI-AS normal (□), and TI-S normal (Δ).
Figure 2B:
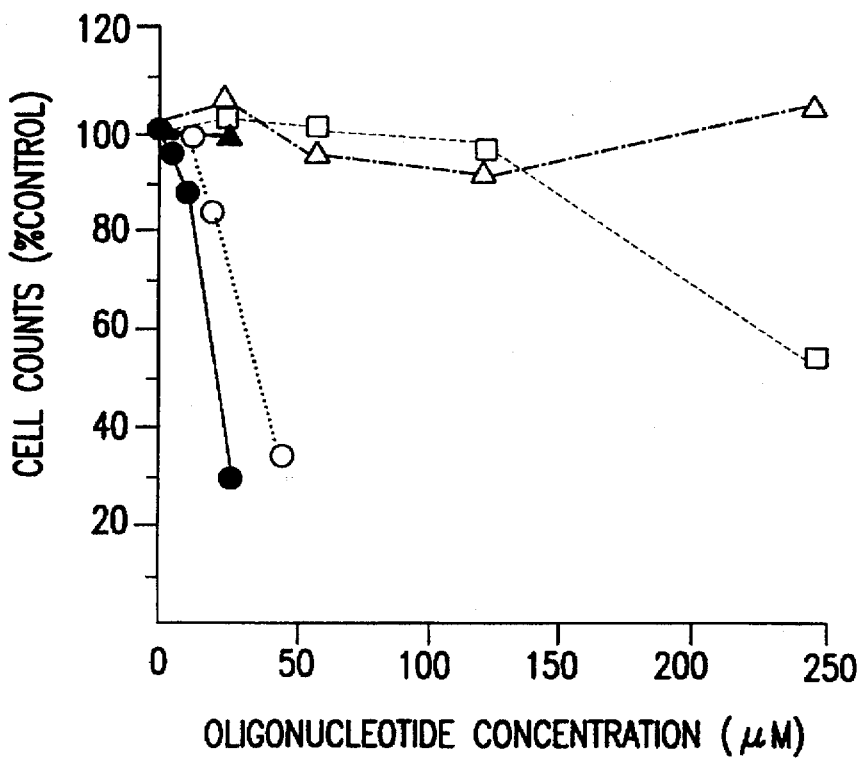

As shown in FIG. 2, TI-AS phosphorothioate oligodeoxynucleotides markedly inhibited the proliferation of 697 cells at 25–50 µM. In contrast, normal TI-AS oligodeoxynucleotides required concentrations 5–10-fold higher (approximately 250 µM) to cause a comparable suppression of 697 cellular proliferation. Suppression by the antisense phosphorothioate oligodeoxynucleotide TI-AS was specific over this concentration range, since its complementary sense oligodeoxynucleotide (TI-S) produced little inhibition of 697 cell growth in replicate cultures (see FIG. 2).

Influence of Serum Preparation on Inhibition by Antisense Phosphorothioate Oligodeoxynucleotides To further define the effects of serum preparation on the inhibitory activity of phosphorothioate oligodeoxynucleotides, FBS that had been heated to 56° C. for 30 minutes, 68° C. for 1 hour, or not heated prior to addition to cultures was added to cultures of RS11846 lymphoma cells.

RS11846 cells were cultured in medium containing 1% (vol:vol) HL1-concentrate or 5% (vol:vol) FBS that had been heated at 56° C. for 0.5 hour, 68° C. for 1 hour, or that had not been heated. Cell counts were calculated as a percentage relative to control cultures treated with equivalent concentrations of TI-S phosphorothioate oligodeoxynucleotide, and represent the mean percentage (standard deviation was less than 10% for all values) for duplicate cultures counted on days 4 and 5.

The TI-AS phosphorothioate oligodeoxynucleotide completely inhibited the growth of RS11846 cells at 25 µM, with an estimated half-maximal inhibitory concentration of approximately 11 µM. In contrast, this phosphorothioate oligodeoxynucleotide was considerably less effective in cultures containing 5% (v:v) FBS. Furthermore, heating FBS prior to adding it to cultures did not significantly improve the ability of the TI-AS phosphorothioate oligodeoxynucleotide to suppress the growth of RS11846 lymphoma cells. At an oligodeoxynucleotide concentration of 50 µM, inhibition of proliferation of RS11846 cells never exceeded 48% in serum-containing cultures, regardless of the heating procedure used.

Influence of Dialysis of Serum on Inhibition by Normal and Phosphorothioate Antisense Oligodeoxynucleotides To further characterize the nature of the interfering substances in serum, experiments were performed wherein 68° C.-heated serum was extensively dialyzed (molecular weight cutoff=3500) prior to being added to cultures of 697 leukemic cells. Experiments were conducted with 12.5 µM TI-AS phosphorothioate oligodeoxynucleotide and 200 µM of the normal oxygen-based TI-AS oligodeoxynucleotide.

697 cells were cultured in medium containing 1% (vol:vol) HL1-concentrate (A) or 5% (vol:vol) of three different lots of 68° C.-treated FBS (B,C,D). Each serum preparation was contrasted before (ND) and after (D) extensive dialysis. TI-AS (+) and TI-S (−) oligodeoxynucleotides were added to replicate cultures at 200 µM for normal oxygen-based oligodeoxynucleotides (OXY) and at 12.5 µM for phosphorothioate oligodeoxynucleotides (PT). Relative levels of DNA synthesis (kcpm) were measured after 2 or 4 days of culture for normal and phosphorothioate oligodeoxy-nucleotides, respectively.

For the three different lots of FBS tested, two exhibited little change after dialysis in cultures containing either normal or phosphorothioate oligodeoxynucleotides. One lot of FBS, however, appeared to interfere less with the inhibitory activities of these antisense oligodeoxynucleotides after dialysis.

Experiments with Stably Transfected NIH 3T3 Cells

Though the antisense oligodeoxynucleotides described herein were designed to block bcl-2 mRNA translation (TI-AS) and splicing (SD-AS), the molecular mechanisms of their actions are not yet known. To determine the effect of formation of oligodeoxynucleotide-RNA hybrids within cells upon inhibition of cellular growth, irrespective of the nucleotide sequence, cells transformed to express human bcl-2 cDNA transcripts were cultured with normal oligodeoxynucleotides.

200 µM of normal TI-AS and TI-S oligodeoxynucleotide were added to cultures of typical NIH 3T3 cells and to cultures of these cells that had been stably transfected with expression constructs that produce high levels of human bcl-2 cDNA transcripts for either the usual sense (3T3-alpha-S cells) or the antisense (3T3-alpha-AS cells) strand.

For RNA blot analyses, polyadenylated mRNA was purified from normal NIH 3T3 cells and from cells stably transfected with expression constructs that produce either sense (3T3-alpha-S) or antisense (3T3-alpha-AS) recombinant bcl-2-alpha mRNAs, according to the method of 13. Approximately 5 µg of mRNA was subjected to RNA blot analysis, essentially as described in (16), using either $^{32}P$-labeled hybridization probes derived from human or murine bcl-2 sequences.

An autoradiogram resulting from a one-day exposure of a blot containing RNAs from normal 3T3 cells, 3T3-alpha-AS cells, and 3T3-alpha-S cells showed high relative levels of recombinant 2.4 and 1.4 kbp bcl-2 transcripts produced from the bcl-2 expression constructs that were transfected into 3T3-alpha-AS and 3T3-alpha-S cells.

A 10-day exposure of a blot containing RNA from normal 3T3 cells that were either proliferating or quiescent at the time of harvesting RNA showed low but detectable levels of normal 7.5 and 2.4 kbp murine bcl-2 transcripts present in proliferating 3T3 cells.

TI-AS oligodeoxynucleotide specifically suppressed DNA synthesis and cellular replication in cultures of normal NIH 3T3 cells, consistent with findings by others that fibroblasts do contain bcl-2 transcripts, albeit at low levels. The TI-AS oligodeoxynucleotide disclosed herein is complementary to the mouse bcl-2 sequence in 18 of its 20 bases (17), accounting for its ability to suppress the growth of murine NIH 3T3 cells.

NIH 3T3 cells, 3T3-alpha-AS cells, and 3T3-alpha-S cells were cultured in medium containing 5% (vol:vol) 68° C.-treated serum and either HBSS, 200 µM TI-S normal oligodeoxynucleotide, or 200 µM TI-AS normal oligodeoxynucleotide. Relative levels of DNA synthesis (kcpm) were measured in cultures after 3 days and reflect a 16 hour incubation with 0.5 µCi/well of [$^3$H]-thymidine. Cell densities, estimated by phase microscopy, were consistent with the measured DNA synthesis in cultures. The percentage of inhibition of DNA synthesis in cultures containing TI-AS oligodeoxynucleotides was calculated relative to control cultures containing HBSS.

As with normal NIH 3T3 cells, culturing 3T3-alpha-S cells (producing human bcl-2-alpha sense transcripts) with TI-AS and TI-S oligodeoxynucleotides demonstrated specific suppression, since the sense oligodeoxynucleotide TI-S was not inhibitory. The level of inhibition of cellular proliferation by the antisense oligodeoxynucleotide, however, was not as great in 3T3-alpha-S cells, as might be expected, since these cells contain more bcl-2 mRNA.

Adding TI-S oligodeoxynucleotide to cultures of 3T3-alpha-AS cells (produce antisense bcl-2 transcripts) ruled out inhibition of cellular growth through a nonspecific mechanism involving oligodeoxynucleotide-RNA hybrid formation. The TI-S oligodeoxynucleotide caused little suppression of 3T3-alpha-AS cell proliferation, whereas the TI-AS oligodeoxynucleotide was markedly inhibitory in these cells. Similar data were obtained with TI-AS and TI-S phosphorothioate oligodeoxynucleotides.

Measurements of DNA Fragmentation As An Indicator Of bcl-2 Antisense Oligodeoxynucleotide-Mediated Programmed Cell Death In Human Lymphoma Cells Oligonucleotides having the sequences shown in Table 2 were tested for the ability to induce programmed cell death (DNA fragmentation) in the human t (14:18)-containing human lymphoma cell line RS11846. The oligonucleotides were all phosphodiesters, and were targeted against the translation initiation site or the 5'-cap region of bcl-2 mRNAs. Control oligonucleotides included a bcl-2 sense version (TI-S) of TI-AS (having SEQ ID NO: 7) and a scrambled version of TI-AS that has the same base composition, but with jumbled nucleotide order.

TABLE 2

| SEQUENCE | SEQ ID NO: |
|---|---|
| CGCGTGCGAC CCTCTTG | 8 |
| TACCGCGTGC GACCCTC | 9 |
| TCCTACCGCG TGCGACC | 10 |
| CCTTCCTACC GCGTGCG | 11 |
| GACCCTTCCT ACCGCGT | 12 |
| GGAGACCCTT CCTACCG | 13 |
| GCGGCGGCAG CGCGG | 14 |
| CGGCGGGGCG ACGGA | 15 |
| CGGGAGCGCG GCGGGC | 16 |

RS11846 cells were adapted to grow in HL1 media with 1% FCS and their DNA metabolically labeled by addition of $^{125}$I-deoxyuridine to cultures for three hours. Labeled cells were then washed thoroughly and cultured for two days in the presence of various oligonucleotides at 50 µM. Cells were then recovered from 200 µL cultures by centrifugation, and lysed in a hypotonic buffer containing 10 mM EDTA and 1% Triton X100. After centrifugation at 16,000 xg to pellet unfragmented genomic DNA, the supernatant fraction containing fragmented DNA was extracted with phenol/chloroform and ethanol precipitated. This DNA was then subjected to gel electrophoresis in 1.5% agarose gel and transferred to nylon membranes for autoradiography.

Figure 3:
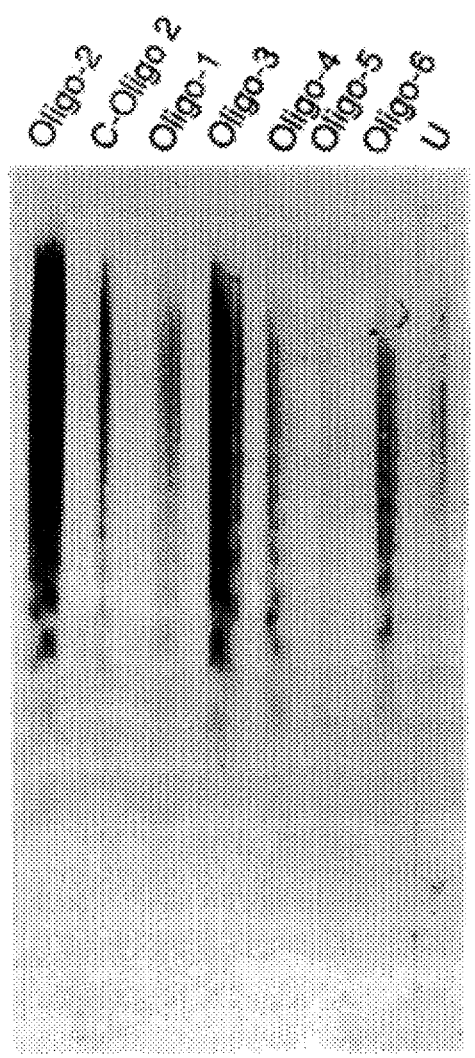
FIG. 3 shows the results of gel electrophoresis of six antisense oligonucleotides targeted against the translation initiation site of bcl-2 mRNA.
Figures 4A, 4B:
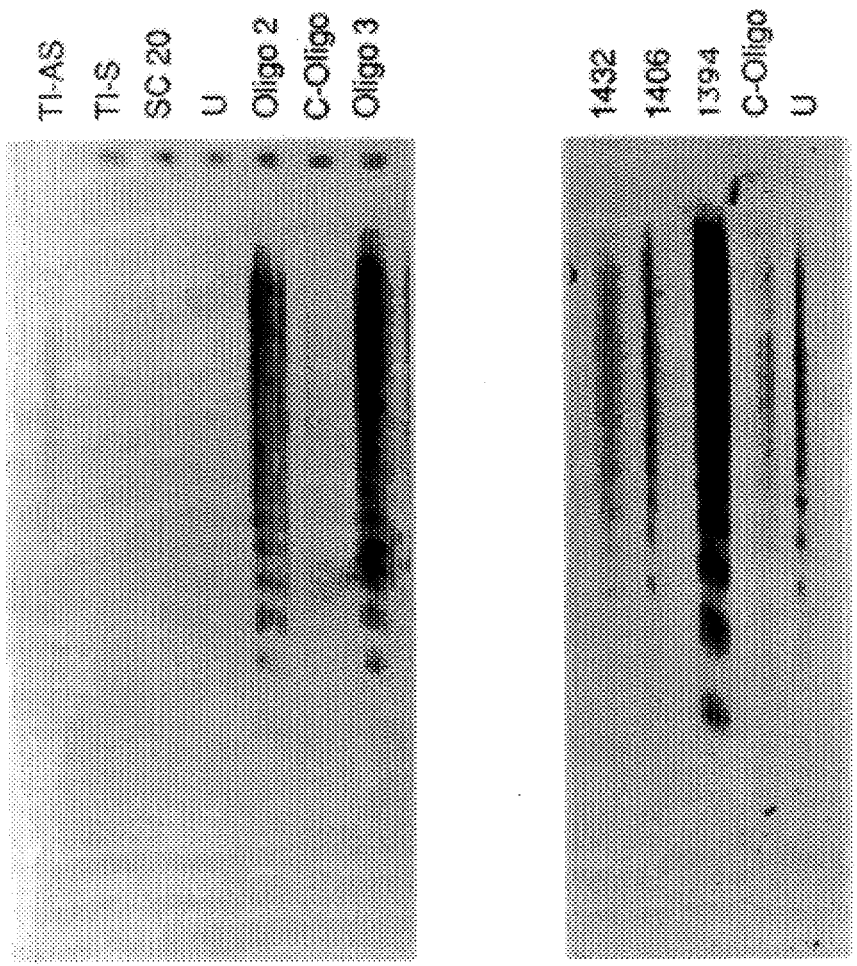
FIG. 4 shows the degree of DNA fragmentation resulting from oligonucleotide treatment of RS11846 cells.

The results of two experiments are shown in FIGS. 3 and 4. The six bcl-2 antisense oligonucleotides targeted in the vicinity of the ATG site of translation initiation in bcl-2mRNAs were tested. "C-Oligo-2" refers to an oligonucleotide with 4 purposeful mismatches. "U" indicates untreated control cells. FIG. 4 shows the results for the oligonucleotides shown in FIG. 3. "Sc20" refers to a 20 mer with the same base composition as TI-AS, but with scrambled sequence. FIG. 4(b) shows the results for three oligonucleotides targeted against the 5'-cap of bcl-2 mRNAs. The numbers refer to the distance of these oligomers from the ATG-translation initiation site.

The presence of a ladder of DNA fragments (unit size of approximately 200 bp) is indicative of programmed cell death. At 50 µM, TI-AS caused little DNA fragmentation, whereas the oligonucleotides having SEQ ID NO: 9 and SEQ ID NO: 10, and one of the 5'-cap oligonucleotides (SEQ ID NO: 14) led to pronounced DNA fragmentation.

Figure 5:
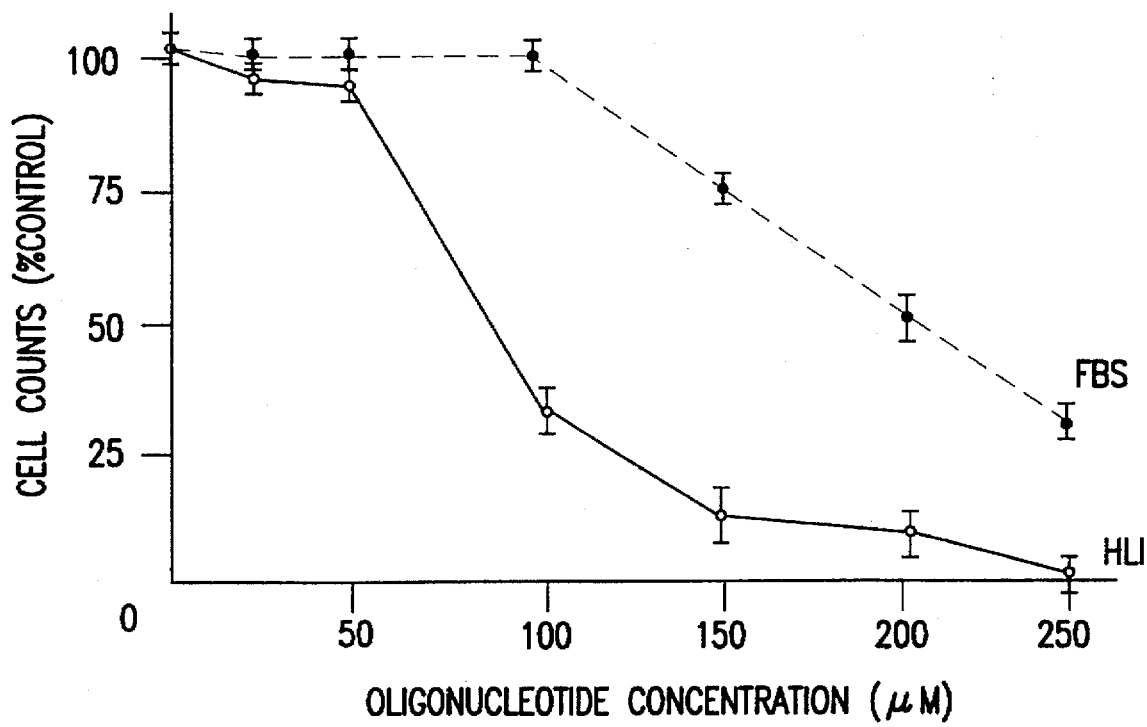
FIG. 5 is a graph showing the concentration-dependence of inhibition by an antisense oligonucleotide targeted against the translation initiation site of bcl-2 mRNA.

Concentration-Dependence of Inhibition by Antisense Phosphodiester Oligodeoxynucleotides in Serum-Free Cultures 697 pre-B cell leukemia cells were cultured in medium with either 1% (vol:vol) HL-1 concentrate (serum-free conditions [o] or 5% (vol:vol) 68° C.-treated serum (FBS2) [●], see FIG. 5. Shown are cellular densities measured after 2 days in cultures containing various concentrations of phosphodiester TI-AS oligodeoxynucleotide. Data are shown as percentages relative to control cultures treated with a sense oligonucleotide, and reflect the mean ± standard deviation for duplicate samples.

Immunofluorescence Analysis of bcl-2 Protein Levels in Oligodeoxynucleotide-Treated 697 Cells For studies with oligodeoxynucleotides, $0.25 \times 10^4$ (for phosphorothioate) or $0.5 \times 10^6$ (for normal oligodeoxynucleotides), 697 cells were cultured in 1 ml of HL-1 serum-free medium in 24 well culture dishes (Linbro. Flow Lab. Inc.). After 2 days (for normal) or 4 days (for phosphorothioates), cells were recovered from cultures, washed once in PBS-A [PBS, pH 7.4 (Gibco)-0.1% bovine serum albumin-0.1% sodium azide], and fixed for 5–10 minutes on ice in 1% paraformaldehyde/PBS solution. The cells were then washed once in PBS and incubated in 1 ml of absolute methanol at −20° C. for 10 minutes. After washing once in PBS-A, cells were then resuspended in PBS containing 0.05% Triton-X100 for 3 minutes on ice, washed in PBS-A and preblocked for 30 minutes at 4° C. in PBS with 10% (v/v) heat-inactivated goat serum.

For addition of the first antibody, preblocked cells were resuspended in 100 μl of PBS-G (PBS-1% goat serum-0.1% sodium azide) prior to aliquoting 50 μl into separate tubes that contained 1 μl of either BCL2 antibody (Halder et al., Nature (London), 342:195–197 (1989)) or affinity-purified normal rabbit control IgG (Cappel 6012-0080) and incubated for 1 hour on ice. The BCL2 antibody used for these studies was prepared in rabbits using a synthetic peptide corresponding to amino acids (98–114) of the BCL2 protein and was affinity-purified by protein-A-Sepharose chromatography and used at approximately 1 mg/ml. Cells were then washed in PBS-A and incubated in 0.5–1.0 ml PBS-A for 15–20 minutes on ice to allow diffusion of nonspecific cell-associated antibody prior to resuspending cells in 100 μl of PBS-G containing 5 μg of biotinylated goat anti-rabbit IgG (BA1000; Vector Labs) for 30 minutes. After washing once and incubating for 15 minutes in PBS-A, cells were finally resuspended in 100 μl of PBS-A containing 2 μg of FITC-conjugated avidin (Vector Labs A2011) for 20 minutes and washed three times in PBS-A prior to analysis with an Ortho cytofluorograph 50-H connected to an Ortho 2150 data-handling system. The specificity of this method for detecting BCL2 protein was confirmed by immunofluorescence microscopy (showing cytosolic staining), peptide competition, and studies of cell lines that expressed various levels of BCL2mRNA and proteins through gene transfer manipulations.

For measurements of surface HLA-DR antigen expression, an indirect immunofluorescence assay method was used (Reed et al., J. Immunolo, 134:1631–1639 (1985)) involving incubation of viable cells with a murine anti-HLA-DR monoclonal antibody (IgG2a)(Becton-Dickinson 7360) or a negative control antibody, R3-367 (IgG2a), followed by FITC-conjugated goat anti-mouse IgG (Cappel 1711-0081). Cells were fixed in 1% paraformaldehyde/PBS prior to FACS analysis.

697 cells were cultured for 2 days (PO) or 4 days (PS) with various oligonucleotides. In FIG. 6, the black columns show the results with a sense oligonucleotide, and the hatched columns with an antisense oligonucleotide TI-AS. Cells were labeled with anti-bcl-2 antiserum and analyzed by FACS. Data are expressed as percentages relative to the mean fluorescence obtained with untreated 697 cells.

FIG. 7 shows typical FACS results obtained for 697 cells before and after treatment with 100 μM PO bcl-2 antisense oligonucleotides. A: untreated 697 cells labeled with either anti-bcl-2 antiserum (hatched area) or normal rabbit serum control (white area); B: untreated 697 cells labeled with either anti-HLA-DR antibody (hatched area) or a negative control antibody (white area); C: 697 cells cultured for 2 days with either normal bcl-2 TI-AS (white area) or TI-AS (hatched area) oligodeoxynucleotides and labeled with anti-bcl-2 antibody; D: 697 cells cultured with TI-AS and TI-S oligodeoxynucleotides (as in C), but labeled with anti-HLA-DR antibody.

Figure 6A:
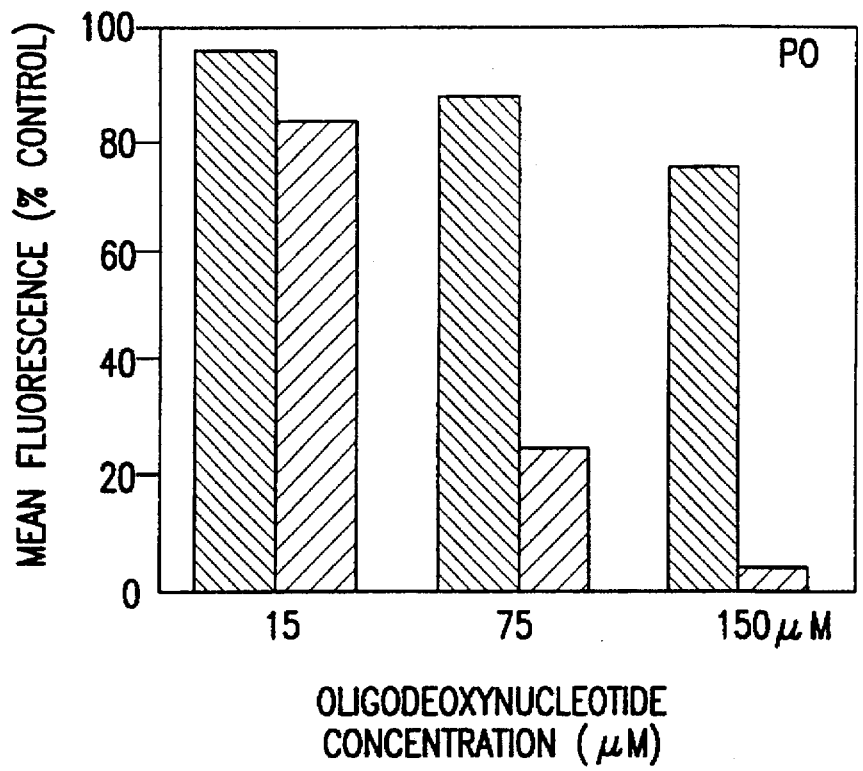
Figure 6B:
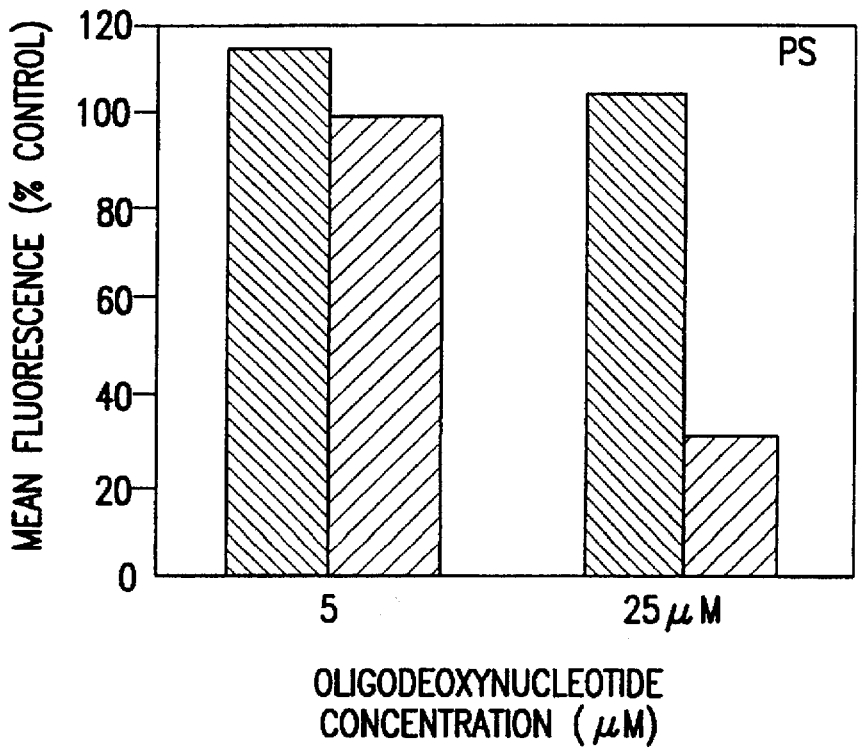
Figure 7A:
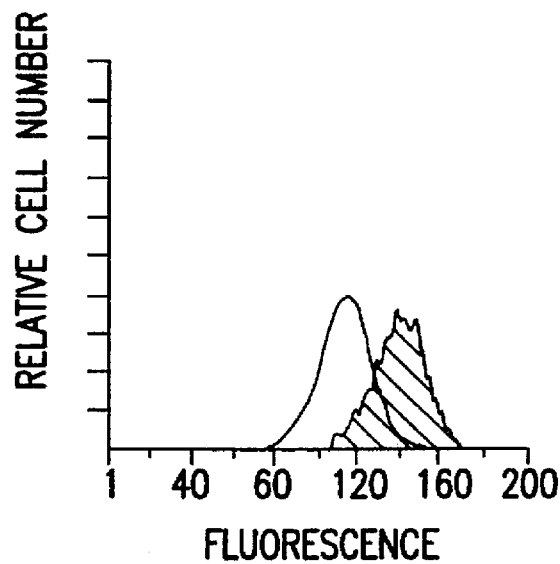
Figure 7B:
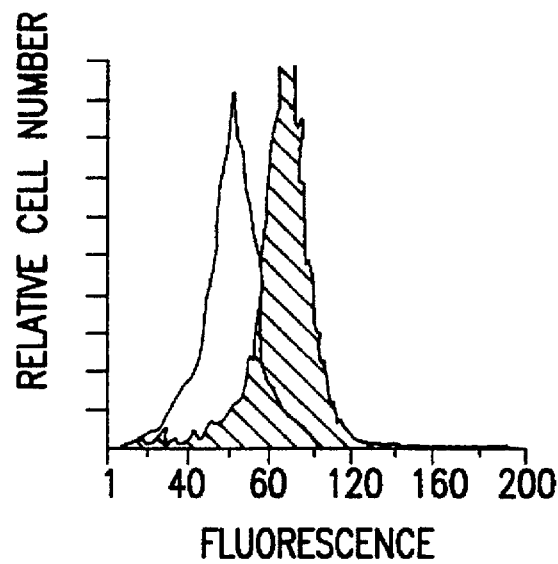
Figure 7C:
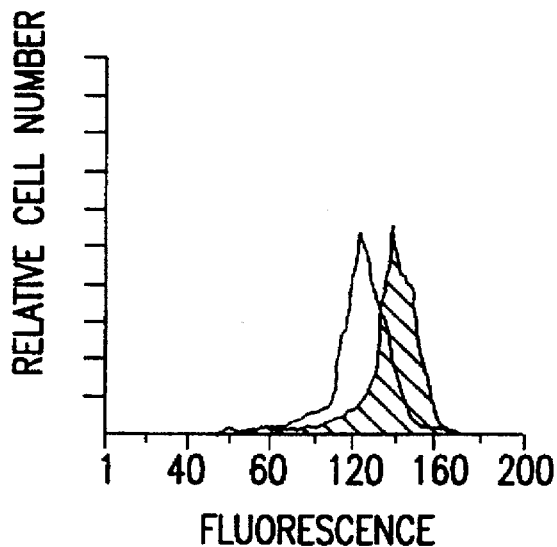
Figure 7D:
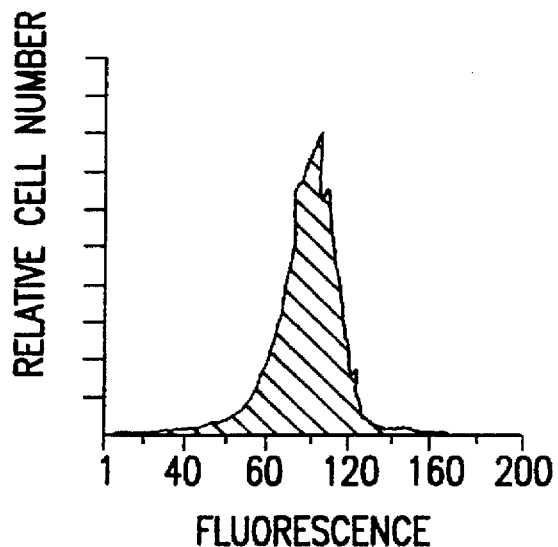

As shown in FIGS. 6 (a) and (b), PO and PS bcl-2 antisense oligonucleotides produced specific concentration-dependent reductions in the levels of bcl-2 proteins, without altering the levels of expression of HLA-DR (FIG. 7) and other control antigene. At 150 μM, for example, PO antisense oligodeoxynucleotide caused an approximately 75–95% reduction in bcl-2 fluorescence, whereas the control sense oligodeoxynucleotide diminished bcl-2 protein levels by only 10–20% (FIG. 6(a)). Similarly, cultured 697 cells for 4 days with the PS antisense oligodeoxynucleotide ar 25 μM resulted in approximately 70% reduction in bcl-2 fluorescence. In comparison, the sense PS oligodeoxynucleotide TI-AS inhibited bcl-2 protein levels by only approximately 15%, as measured by this assay (FIG. 6(b)).

SIGNIFICANCE

In phosphorothioate oligodeoxynucleotides one of the non-bridging oxygen atoms in each internucleotide phosphate linkage is replaced by a sulfur atom. This modification renders phosphorothioate oligodeoxynucleotides extremely resistant to cleavage by nucleases, Stein et al., Nucl. Acids Res., 16:3209–3221 (1988). Despite the substitution of a sulfur atom for an oxygen, phosphorothioate oligodeoxynucleotides retain good solubility in aqueous solutions; hybridize well, though with some decrease in the melting temperature of RNA-oligodeoxynucleotides duplexes; and are synthesized conveniently by the widely employed method of automated oligodeoxynucleotides synthesis with phosphoroamidites.

Antisense bcl-2 phosphorothioate oligodeoxynucleotides have been found to be more potent inhibitors of leukemic cell grown than their normal oxygen-based counterparts. When tested under serum-free conditions, these oligodeoxynucleotides reduced cellular proliferation by half at concentrations of approximately 15–25 μM, whereas the normal oligodeoxynucleotide achieved 50% inhibition at 125–250 μM. This finding may be explained by the reduced sensitivity of phosphorothioate oligodeoxynucleotides to cellular nucleases, or may be attributable to other mechanisms. For example, mRNAs hybridized with phosphorothioate oligodeoxynucleotides may experience enhanced degradation through a mechanism involving an RNAse H-like activity.

Despite their increased inhibitory activity, phosphorothioate antisense oligodeoxynucleotides retained sequence-specificity. At the concentrations tested (less than 25 μM), sense versions of these oligodeoxynucleotides had little effect on leukemic cell growth. Both normal and phosphorothioate antisense oligodeoxynucleotides appeared to initially suppress the proliferation of leukemic cells through non-cytotoxic mechanisms. During the first few days of culture, cellular replication was inhibited without a concomitant rise in cell death. Later in these cultures (days 4–5 for normal oligodeoxynucleotides, days 6–8 for phosphorothioates), however, cellular viabilities declined.

Comparing the kinetics of inhibition by normal and phosphorothioate oligodeoxynucleotides revealed that the latter compounds have a slower onset of action. Maximal inhibition of leukemic cell proliferation by normal antisense oligodeoxynucleotides occurred two days after initiation of cultures, whereas phosphorothioate oligodeoxynucleotides required 4 to 7 days to achieve maximal inhibition.

The usefulness of antisense oligodeoxynucleotides in inhibiting human lymphoma/leukemia cells that express the bcl-2 gene has been shown by the examples herein. Antisense oligodeoxynucleotides complementary to at least an effective portion of the mRNA of the human bcl-2 gene has been found to inhibit proliferation of RS11846 human follicular lymphoma cells (t (14;18) chromosomal translocation and high bcl-2 expression), 697 human pre B cell leukemia cells (high bcl-2 expression), JURKAT human acute lymphocytic leukemia cells (medium bcl-2 expression), normal human lymphocytes (medium bcl-2 expression) and murine fibroblasts (low bcl-2 expression). Although bcl-2 antisense reagents can suppress the growth of many types of cells, the t (14;18)-containing lymphoma and leukemia cells seem to be the most sensitive, allowing for specific inhibition of malignant cells.

A variety of chemically modified forms of DNA can be employed in the instant invention. For example, phosphorothioates and methylphosphonates have been found to be useful in the present invention.

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Synthetic DNA ( i v ) ANTI-SENSE: YES ( x i ) SEQUENCE DESCRIPTION: SEQ ID NO:1:

```
CAGCGTGCGC CATCCTTCCC                                             20
```

( 2 ) INFORMATION FOR SEQ ID NO:2:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:2:

```
CTTTCCTCT GGGAAGGATG GCGCACGCTG GGAGA                             35
```

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Synthetic DNA ( i v ) ANTI-SENSE: YES ( x i ) SEQUENCE DESCRIPTION: SEQ ID NO:3:

```
GATGCACCTA CCCAGCCTCC                                             20
```

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:4:

ACGGGGTACG GAGGCTGGGT AGGTGCATCT GGT                33

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Synthetic DNA ( i v ) ANTI-SENSE: YES ( x i ) SEQUENCE DESCRIPTION: SEQ ID NO:5:

ACAAAGGCAT CCTGCAGTTG                                20

( 2 ) INFORMATION FOR SEQ ID NO:6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:6:

CCCCCAACTG CAGGATGCCT TTGTGGAACT GTACGG              36

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Synthetic DNA ( i v ) ANTI-SENSE: NO ( x i ) SEQUENCE DESCRIPTION: SEQ ID NO:7:

GGGAAGGATG GCGCACGCTG                                20

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Synthetic DNA ( i v ) ANTI-SENSE: YES ( x i ) SEQUENCE DESCRIPTION: SEQ ID NO:8:

GTTCTCCCAG CGTGCGC                                   17

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Synthetic DNA ( i v ) ANTI-SENSE: YES ( x i ) SEQUENCE DESCRIPTION: SEQ ID NO:9:

CTCCCAGCGT GCGCCAT　　　　　　　　　　　　　　　　　　　　　　　　　　　　17

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Synthetic DNA ( i v ) ANTI-SENSE: YES ( x i ) SEQUENCE DESCRIPTION: SEQ ID NO:10:

CCAGCGT GCGCCATCCT　　　　　　　　　　　　　　　　　　　　　　　　　　　　17

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Synthetic DNA ( i v ) ANTI-SENSE: YES ( x i ) SEQUENCE DESCRIPTION: SEQ ID NO:11:

GCGTGCG CCATCCTTCC　　　　　　　　　　　　　　　　　　　　　　　　　　　　17

( 2 ) INFORMATION FOR SEQ ID NO:12:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Synthetic DNA ( i v ) ANTI-SENSE: YES ( x i ) SEQUENCE DESCRIPTION: SEQ ID NO:12:

TGCGCCA TCCTTCCCAG　　　　　　　　　　　　　　　　　　　　　　　　　　　　17

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
      ( A ) DESCRIPTION: Synthetic DNA ( i v ) ANTI-SENSE: YES ( x i ) SEQUENCE DESCRIPTION: SEQ ID NO:13:

GCCATCC TTCCCAGAGG     17

( 2 ) INFORMATION FOR SEQ ID NO:14:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Synthetic DNA ( i v ) ANTI-SENSE: YES ( x i ) SEQUENCE DESCRIPTION: SEQ ID NO:14:

GGCGC GACGGCGGCG     15

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Synthetic DNA ( i v ) ANTI-SENSE: YES ( x i ) SEQUENCE DESCRIPTION: SEQ ID NO:15:

AGGCA GCGGGGCGGC     15

( 2 ) INFORMATION FOR SEQ ID NO:16:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Synthetic DNA ( i v ) ANTI-SENSE: YES ( x i ) SEQUENCE DESCRIPTION: SEQ ID NO:16:

CGGGCG GCGCGAGGGC     16

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Synthetic DNA ( x i ) SEQUENCE DESCRIPTION: SEQ ID NO:17:

TCTCCCAGCGT GCGCCAT     18

What is claimed is:

1. An antisense oligonucleotide complementary to BCL-2 mRNA consisting of from 10 to 35 bases and complementary to at least 10 consecutive bases of SEQ ID NO: 2.

2. The antisense oligonucleotide of claim 1, wherein said oligonucleotide has 10 to 20 bases.

3. The antisense oligonucleotide of claim 1, wherein said oligonucleotide has 20 to 35 bases.

4. The antisense oligonucleotide of claim 1, which consists of from 10 to 18 bases and which is complementary to SEQ ID NO: 2.

5. The antisense oligonucleotide of claim 1, which is a phosphorothioate derivative.

6. An antisense oligonucleotide having the nucleotide sequence of SEQ ID. NO: 1, 3, 5, 9, 10 or 14.

7. The antisense oligonucleotide of claim 6, which is a phosphorothioate derivative.

8. The antisense oligonucleotide of claim 6, whose sequence is SEQ ID NO: 1.

9. The antisense oligonucleotide of claim 6, whose sequence is SEQ ID NO: 3.

10. The antisense oligonucleotide of claim 6, whose sequence is SEQ ID NO: 5.

11. The antisense oligonucleotide of claim 6, whose sequence is SEQ ID NO: 9.

12. The antisense oligonucleotide of claim 6, whose sequence is SEQ ID NO: 10.

13. The antisense oligonucleotide of claim 6, whose sequence is SEQ ID NO: 14.

* * * * *

UNITED STATES PATENT AND TRADEMARK OFFICE
CERTIFICATE OF CORRECTION

PATENT NO : 5,734,033
DATED : March 31, 1998
INVENTOR(S) : John REED

It is certified that error appears in the above-identified patent and that said Letters Patent is hereby corrected as shown below:

In Column 23, lines 39 through 48, please delete in its entirety:

"(2) INFORMATION FOR SEQ ID NO: 17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear

(ii) MOLECULE TYPE: other nucleic acid
        (A) DESCRIPTION: Synthetic DNA

(xi) SEQUENCE DESCRIPTION: SEQ ID NO:17:

TCTCCCAGCGT     GCGCCAT"

Signed and Sealed this

Eleventh Day of July, 2000

*Attest:*

Q. TODD DICKINSON

*Attesting Officer*      *Director of Patents and Trademarks*